United States Patent [19]
Schaerf

[11] Patent Number: 5,409,469
[45] Date of Patent: Apr. 25, 1995

[54] INTRODUCER SYSTEM HAVING KINK RESISTANT SPLITTABLE SHEATH

[75] Inventor: Raymond Schaerf, Granada Hills, Calif.

[73] Assignee: Medtronic, Inc., Minneapolis, Minn.

[21] Appl. No.: 147,260

[22] Filed: Nov. 4, 1993

[51] Int. Cl.⁶ ............................................. A61M 25/00
[52] U.S. Cl. .................................. 604/282; 604/280; 604/264; 604/160
[58] Field of Search ............... 604/160, 161, 282, 281, 604/280, 264, 164, 171

[56] References Cited

U.S. PATENT DOCUMENTS

| Re. 30,726 | 9/1981 | Otten et al. | 206/601 |
|---|---|---|---|
| 2,685,707 | 8/1954 | Liewellyn et al. | 18/55 |
| 2,752,637 | 7/1956 | Walker et al. | 18/55 |
| 2,776,465 | 1/1957 | Smith | 28/82 |
| 3,008,187 | 11/1961 | Slade | 18/14 |
| 3,034,941 | 5/1962 | Hessenthaler et al. | 154/46 |
| 3,094,122 | 6/1963 | Gauthier et al. | 128/221 |
| 3,382,872 | 5/1968 | Rubin | 128/214.4 |
| 3,404,203 | 10/1968 | Donald | 264/108 |
| 3,545,443 | 12/1970 | Ansari | 128/347 |
| 3,550,591 | 12/1970 | MacGregor | 128/214.4 |
| 3,570,485 | 3/1971 | Riley | 128/214.4 |
| 3,618,613 | 11/1971 | Schulte | 128/348 |
| 3,677,243 | 7/1972 | Nerz | 128/214.4 |
| 3,877,429 | 4/1975 | Rasumoff | 128/214.4 |
| 3,899,283 | 8/1975 | Wallis | 425/461 |
| 4,049,761 | 9/1977 | Lorgé | 264/89 |
| 4,054,136 | 10/1977 | von Zeppelin | 128/214.4 |
| 4,098,406 | 7/1978 | Otten et al. | 206/601 |
| 4,100,393 | 7/1978 | Luther | 219/121 LM |
| 4,306,562 | 12/1981 | Osborne | 128/348 |
| 4,333,460 | 6/1982 | Miller | 128/239 |
| 4,396,574 | 8/1983 | Kovacs | 264/533 |
| 4,449,973 | 5/1984 | Luther | 604/161 |
| 4,451,256 | 5/1984 | Weikl et al. | 604/164 |
| 4,581,025 | 4/1986 | Timmermans | 604/160 |
| 4,596,559 | 6/1986 | Fleischhacker | 604/161 |
| 4,686,996 | 8/1987 | Ulbrich | 128/642 |
| 4,688,554 | 8/1987 | Habib | 604/282 |
| 4,770,443 | 9/1988 | Yamamoto | 285/39 |
| 4,776,846 | 10/1988 | Wells | 604/161 |
| 4,813,425 | 3/1989 | Malis | 128/642 |
| 4,865,593 | 9/1989 | Ogawa et al. | 604/264 |
| 4,874,374 | 10/1989 | Kousai et al. | 604/164 |
| 4,883,468 | 11/1989 | Kousai et al. | 604/164 |
| 4,983,168 | 1/1991 | Moorehead | 604/161 |
| 5,104,388 | 4/1992 | Quackenbush | 604/264 |
| 5,125,904 | 6/1992 | Lee | 604/164 |
| 5,125,909 | 6/1992 | Heinberger | 604/282 |
| 5,146,925 | 9/1992 | Snow | 604/280 |
| 5,167,642 | 12/1992 | Fowles | 604/263 |
| 5,180,372 | 1/1993 | Vegoe et al. | 604/161 |
| 5,180,376 | 1/1993 | Fischell | 604/282 |
| 5,188,605 | 2/1993 | Sleep | 604/160 |
| 5,250,033 | 10/1993 | Evans et al. | 604/160 |
| 5,258,003 | 11/1993 | Liaglia et al. | 604/264 |
| 5,269,755 | 12/1993 | Bodicky | 604/53 |

Primary Examiner—John G. Weiss
Attorney, Agent, or Firm—Michael J. Jaro; Harold R. Patton

[57] ABSTRACT

This invention relates to a flexible kink resistant introducer system for introducing an elongated object into the venous system and especially for introducing a cardiac pacemaker lead. The introducer system features a sheath having a kink resistant section allowing the sheath to be bent in that region and still allow a lead to be introduced therethrough. The kink resistant section comprises a series of bellows or pleats. The bellows or pleats may further be arranged to form a screw about a portion of the sheath to thereby permit the sheath to be screwed into body tissue. The sheath preferably is constructed to readily tear in a longitudinal direction and thus permits the system to be removed from the venous system without having to withdraw the sheath over an end of the pacemaker lead.

37 Claims, 11 Drawing Sheets

INTRODUCER SYSTEM HAVING KINK RESISTANT SPLITTABLE SHEATH

FIELD OF THE INVENTION

This invention relates generally to an introducer system having a kink resistant sheath for the insertion of catheters and other instruments into the body and more particularly to an introducer system having a kink resistant splittable sheath used to introduce pacemaker leads into the venous system.

BACKGROUND OF THE INVENTION

Generally speaking, pacing systems include an implantable pulse generator, commonly known as a pacemaker, electrically connected to the heart by at least one transvenous endocardial lead. More specifically an endocardial lead provides an electrical pathway between the pacemaker, connected to the proximal end of the lead, and endocardial tissue, in contact with the distal end of the lead. Endocardial tissue refers to a specific layer of tissue in the interior of the heart's chambers. In such a manner electrical pulses emitted by the pacemaker travel through the endocardial lead and stimulate the heart.

Endocardial leads are often placed in contact with the endocardial tissue by passage through a venous access, such as the subclavian vein or one of its tributaries. In such a manner transvenous endocardial leads offer as an advantage that they may be placed into contact with the heart without requiring major thoracic surgery. Rather, transvenous endocardial leads may be introduced into a vein and maneuvered therefrom into contact with the heart.

A multi-step procedure is often used to introduce such leads within the venous system. Generally this procedure consists of inserting a hollow needle into a blood vessel, such as the subclavian vein. A wire guide is then passed through the needle into the interior portion of the vessel. The needle is then withdrawn and an introducer sheath and dilator assembly is then inserted over the wire guide into the vessel. The assembly is advanced into a suitable position within the vessel, i.e. so that the distal end is well within the vessel but the proximal end is outside the patient. Next the dilator and wire guide are removed. The introducer sheath is left in position and therefore offers direct access from outside the patient to the interior of the blood vessel. In such a fashion a lead can be passed into the vessel through the introducer sheath and ultimately be positioned within the heart. Finally the introducer sheath is removed from the body. With respect to pacemaker leads, however, which typically have a relatively bulky connector pin assembly at the proximal end, the introducer sheath is removed from the body by being split apart. In such a manner the introducer sheath does not have to be removed over the relatively bulky connector pin assembly at the proximal end of the lead.

An introducer sheath therefore, through its hollow lumen, provides access to the interior of a vessel. A lead introduced into the blood vessel may then moved along the blood vessel until properly positioned within the heart.

To provide such access an introducer sheath must be flexible. Specifically, flexibility permits the introducer sheath to bend and form to a curve compatible with the blood vessel. In such a manner the introducer sheath end is substantially parallel to the blood vessel and a lead which is introduced therethrough is properly oriented along the vessel interior. If the sheath did not conform to the vessel shape, a lead introduced would abut against the vessel wall, possibly injuring the patient and damaging the lead. One problem which may occur, however, due to the flexibility required of the introducer sheath is that the mid-portion of the sheath may form a kink.

Kinking within the introducer sheath may cause serious problems, especially with respect to pacemaker leads. Generally a kink within an introducer sheath is not detected until a lead is attempted to be introduced therethrough. At that time the lead, and in particular the sensitive electrode at the distal end of the lead, strikes the kinked section and is blocked. Continual pushing on the lead may cause damage to the electrode as well as damage to the helical coil and insulative sheath of the lead body. Because such damage may not be readily apparent, implantation of a damaged lead may result, in turn, creating the possibility of serious harm to the patient.

A further problem exists in pacemaker patients who have had multiple leads implanted over time. Scar tissue at the site of implantation has been found to create difficulties with past lead introduction systems. Specifically the relatively tough scar tissue hinders the introduction of a dilator and introducer sheath assembly. Many times, only through use of larger incisions than are otherwise desirable is such an assembly able to be inserted.

SUMMARY OF THE INVENTION

It is an object of the present invention to provide an introducer system having a sheath which is resistant to the formation of kinks.

It is a further object of the invention to provide an introducer system having a kink resistant sheath for introducing an elongated object into the venous system and especially for introducing a cardiac pacemaker lead.

It is a further object of the invention to provide an introducer system having a kink resistant sheath which provides improved insertion through scar tissue.

These objects are met by the present invention which provides an introducer system featuring a sheath having a kink resistant section allowing the sheath to be bent in that region and still allow a lead to be introduced therethrough. The kink resistant section comprises a series of bellows or pleats. The bellows or pleats may be further arranged to form a screw about a portion of the sheath to thereby permit the sheath to be screwed into body tissue. The sheath preferably is constructed to readily split in a longitudinal direction and thus permits the system to be removed from the venous system without having to withdrawn the sheath over an end of the pacemaker lead.

BRIEF DESCRIPTION OF THE DRAWINGS

The foregoing and other aspects of the present invention will be best appreciated with reference to the detailed description of the invention in conjunction with the accompanying drawings, wherein.

DETAILED DESCRIPTION OF THE PREFERRED EMBODIMENT

It is to be understood, that the present invention is not limited to use only in introducing atrial or ventricular pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. For purposes of illustration only, however, the present invention is below described in the context of the introduction of endocardial pacing leads.

Figure 1:
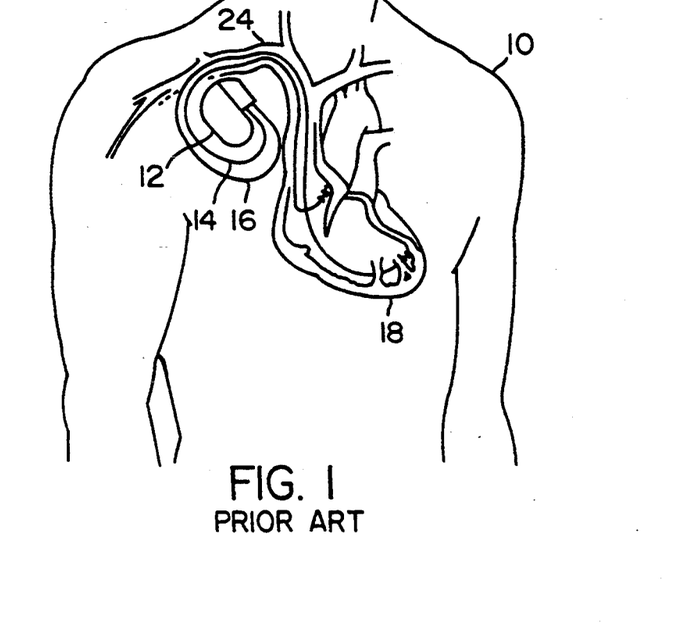
FIG. 1 depicts the venous positioning and placement of transvenous endocardial leads in a patient.

FIG. 1 depicts a typical arrangement of a pacing system implanted in a patient 10, the pacing system comprising a subcutaneously disposed pacemaker 12 and transvenous pacing leads 14 and 16. In FIG. 1, the distal end of pacing lead 14 is shown disposed generally in the atrial region of the patient's heart 18, while the distal end of pacing lead 16 is disposed generally in the ventricular region of heart 18.

The preferred prior art method of lead introduction compatible with an introducer system in accordance with the present invention will be described with reference to FIGS. 2 through 14.

Figure 2:
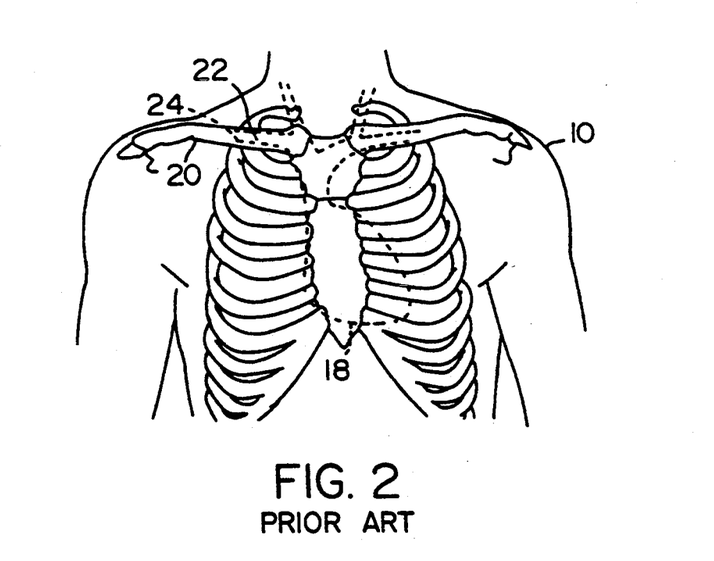
FIG. 2 depicts an appropriate entry site for implantation of a transvenous endocardial lead.

Referring to FIG. 2, and in accordance with common practice in the medical arts, the entry site for a subclavian vein puncture is commonly chosen to be just below and slightly medial to the junction of the middle and inner third of the clavicle 20, at an area designated generally as 22 in FIG. 2. In FIG. 2, the patient's subclavian vein 24 and heart 18 are shown in phantom.

Figure 3:
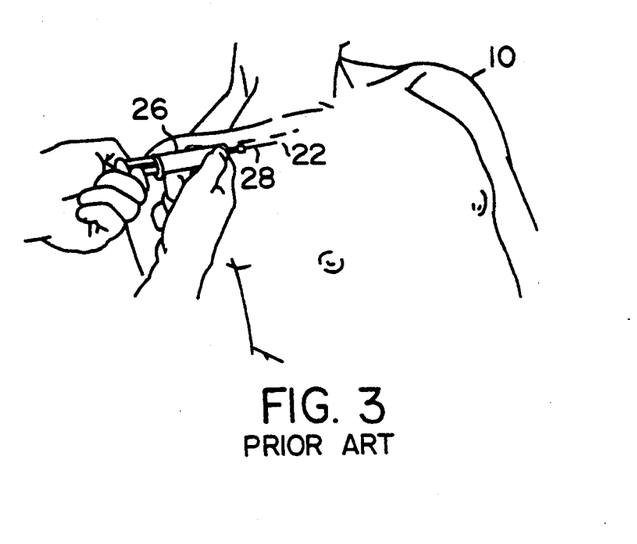
FIGS. 3–14 depict successive stages of introducing a transvenous endocardial lead into a vein.
Figure 4:
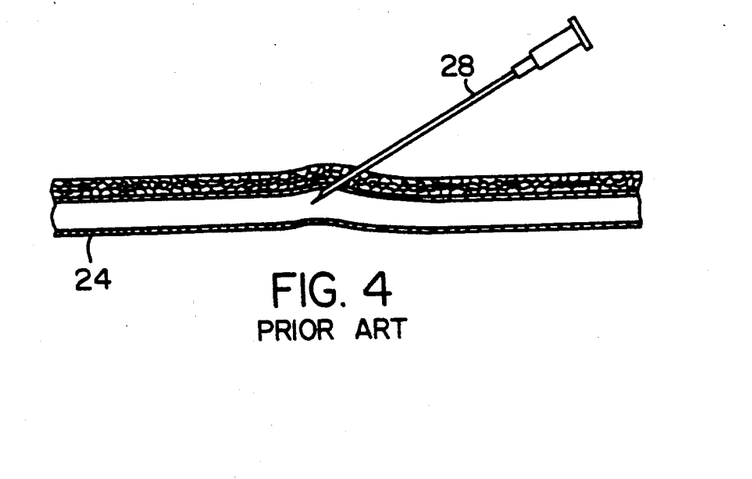

Turning to FIG. 3, the subclavian vein puncture is accomplished by the physician using a disposable syringe 26 having a thin-wall needle 28 detachably connected thereto. Aspiration is performed as the needle is advanced into the subclavian vein, to verify proper needle placement within vessel 24. Next, aspirating syringe 26 is disconnected from needle 28, which remains in vessel 24 as shown in FIG. 4. Typically, the physician will place his or her finger over the needle to avoid air aspiration and excessive bleeding.

Figure 5:
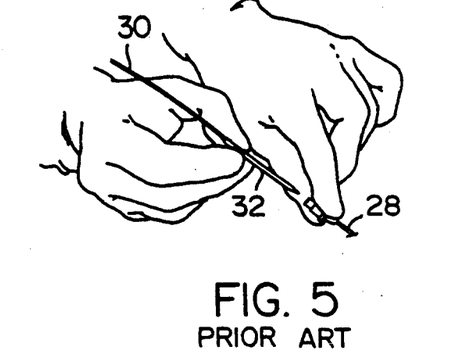
Figure 6:
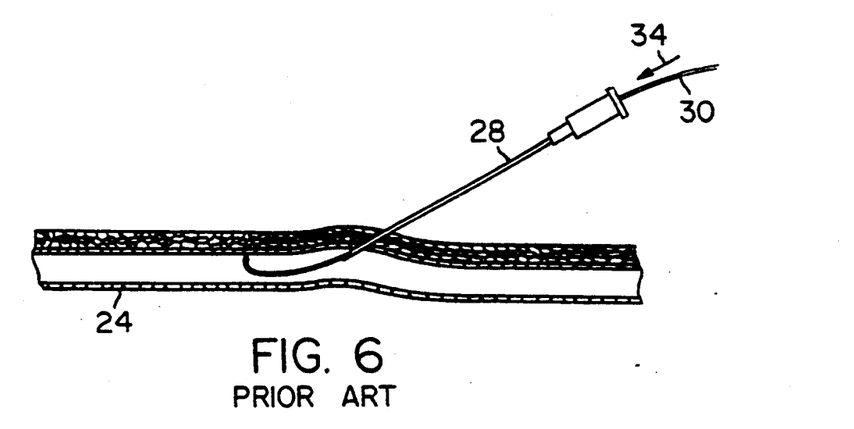
Figure 7:
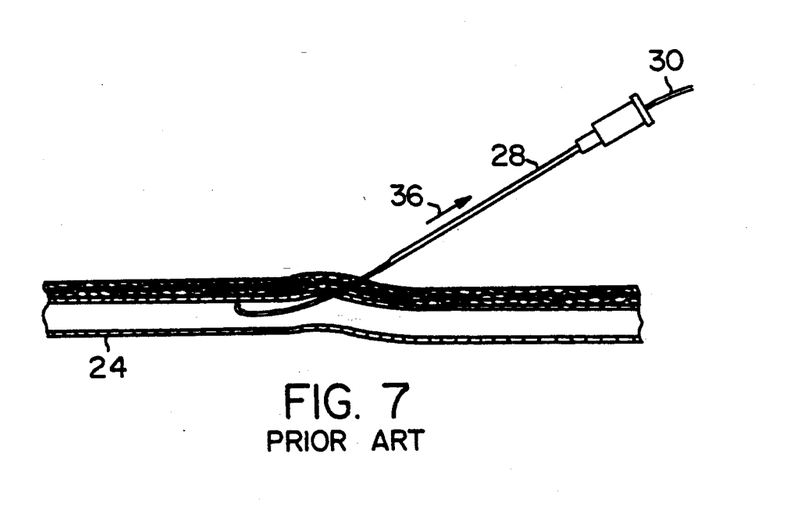

The next step in the lead implantation procedure involves insertion of a conventional J-type guide wire 30 through needle 28, as illustrated in FIG. 5. Typically, guide wire 30 is equipped with a tip deflector 32 for facilitating insertion of wire 30 into the lumen of needle 28. As shown in FIG. 6, as wire 30 is fed through needle 28 in the direction of arrow 34, the distal end of wire 30 exits the tip of needle 28, and wire 30 regains its "J" shape within vessel 24. Once wire 30 has entered vessel 24, needle 28 is withdrawn in the direction of arrow 36 in FIG. 7, leaving wire 30 in place. Wire 30 is advanced along vessel 24 until its distal end is disposed generally in the area of the patient's superior vena cava, leaving approximately 15 to 20-cm of the proximal end of wire 30 exposed.

Figure 8:
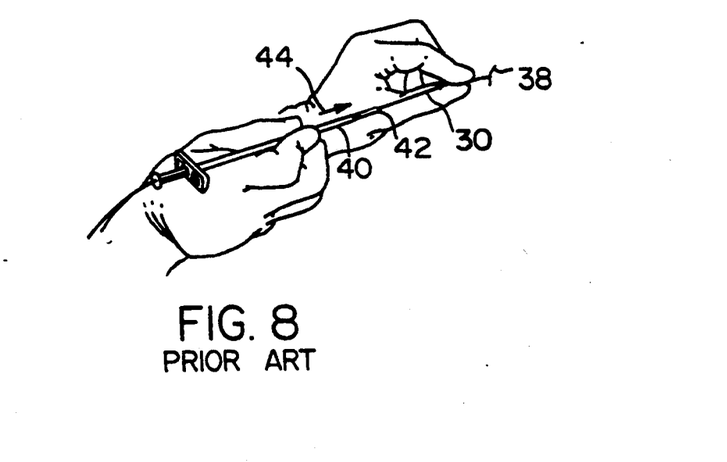
Figure 9:
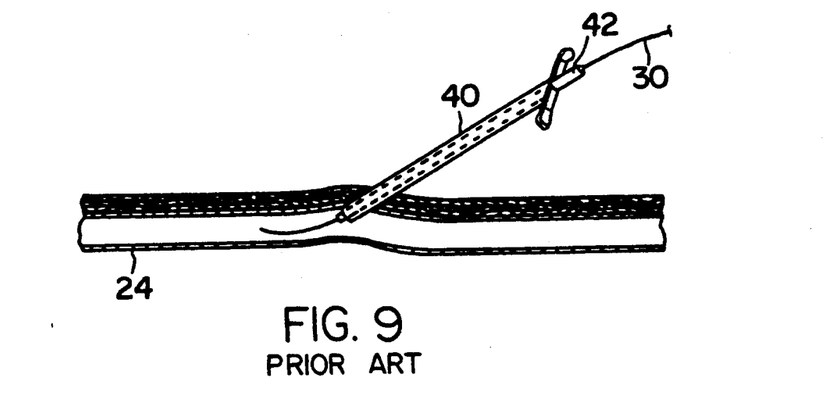

A small skin incision 38 is made at the guide wire entry site, parallel to clavicle 20, as shown in FIG. 8. In the next stage of the implantation procedure, an introducer sheath 40 with tapered vessel dilator 42, as an assembly, are threaded onto the proximal end of wire 30. Sheath 40 and dilator 42 are advanced in the direction of arrow 44, through the subclavian fascia and into subclavian vein 24, until a short length (e.g., 2 to 8-cm) of sheath 40 and vessel dilator 42 remain exposed, as shown in FIG. 9.

Figure 10:
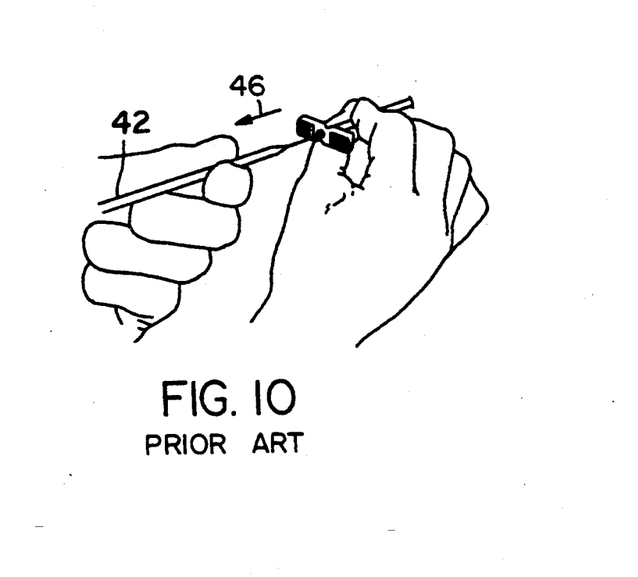
Figure 11:
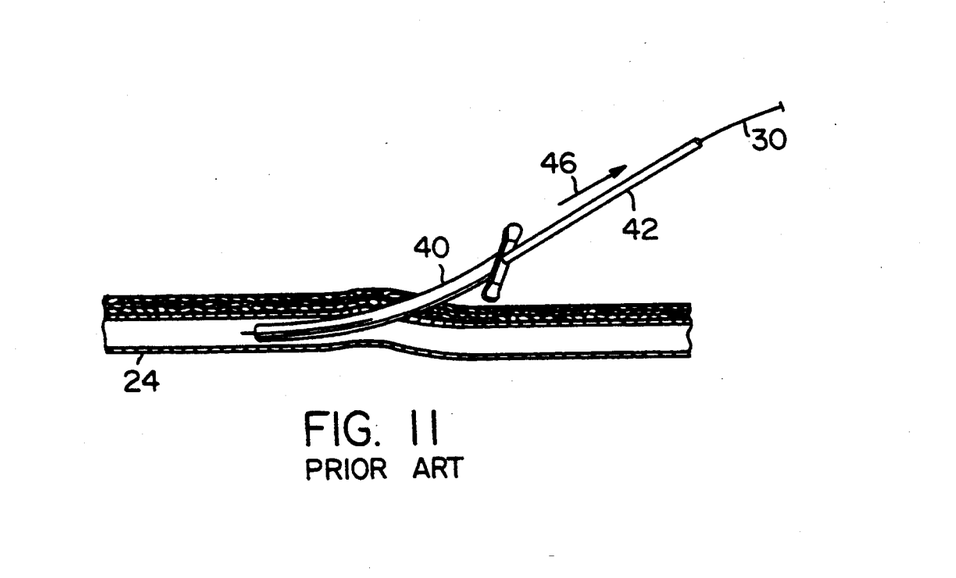

Next, as shown in FIGS. 10 and 11, vessel dilator 42 is withdrawn in the direction of arrow 46 and sheath 40 is introduced further within subclavian vein 24, leaving introducer sheath 40 and guide wire 30 in place with its distal end disposed within subclavian vein 24. Guide wire 30 may be removed at this point as well, although it may be left in place in case the lead needs to be repositioned or reinserted. As shown in FIG. 11, introducer sheath 40 must bend to conform to the shape of subclavian vein 24 to provide an unobstructed conduit for lead 14 to be introduced. Through such curvature, moreover, lead 14 may be introduced so as to be parallel to vein 24 and not abut and damage wall 25 of subclavian vein 24.

Figure 12:
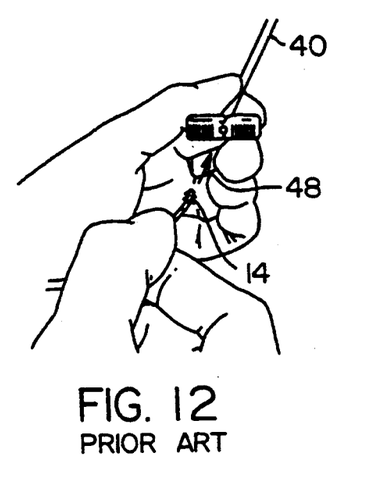
Figure 13:
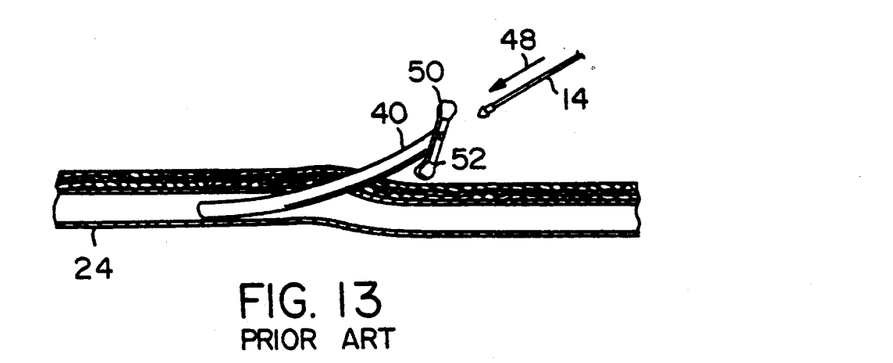
Figure 14:
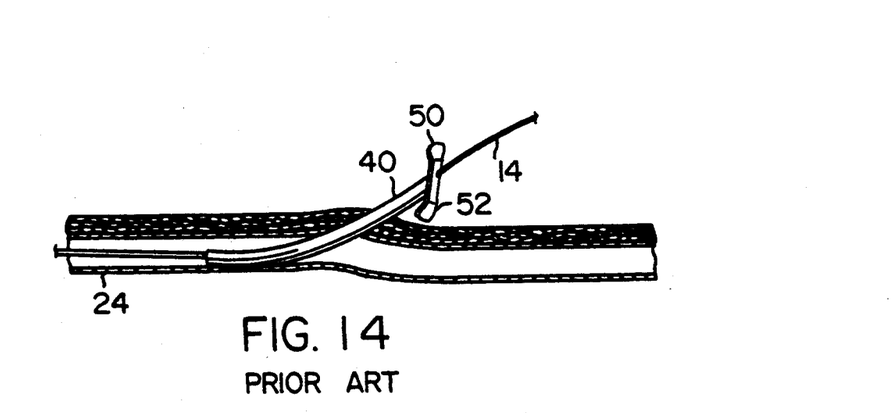

In the final stages of the lead implantation procedure, illustrated in FIGS. 12 through 14, pacing lead 14 is inserted into the proximal end of introducer sheath 40 in the direction of arrow 48, and advanced into the desired position within patient 10 through vessel 24. Lastly, introducer sheath 40 is removed. Removal of introducer sheath 40 may be accomplished in one of several known ways, depending upon the particular type of introducer sheath 40. For example, as disclosed in the above-noted Osborne '562 patent, sheath 40 may be longitudinally split by pulling tabs 50 and 52. Other sheaths are known which are severable by means of a special slitter device or the like.

As shown in FIG. 1, pacemaker 12 may operate in conjunction with two pacing leads. In that case, as with single-lead implants, it may be necessary to keep guide wire 30 in place until after the first lead has been implanted. Thus, as previously noted with reference to FIGS. 10 and 11, guide wire 30 may be left in place when dilator 42 is withdrawn. The first lead, if it is sufficiently small, may be introduced into subclavian vein 24 alongside guide wire 30, and then the first introducer sheath is removed leaving guide wire 30 in place. Then, a second introducer sheath and vessel dilator can be guided along guide wire 30 in the same manner as the first, before guide wire 30 is finally removed.

Figure 15:
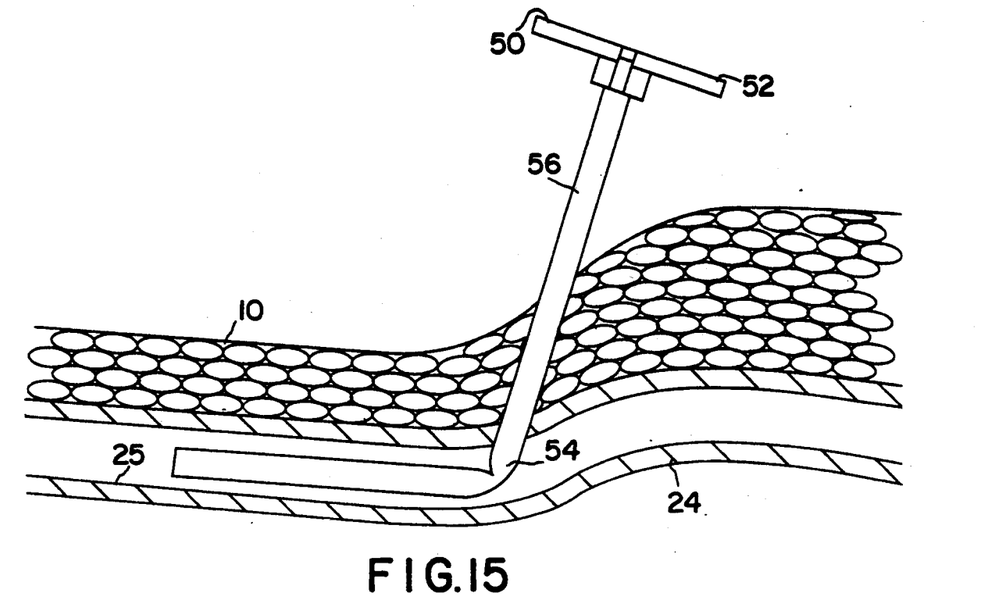
FIG. 15 depicts an introducer sheath used in a body and having a kink.

As depicted in FIG. 15 one problem associated with lead introduction systems and particularly with the sheath used in previous lead introduction systems is the formation of a kink 54. As seen a kink 54 in sheath 56 prevents lead 14 from being introduced therethrough. As mentioned such kinks may be undetected so that a lead inserted into the sheath is blocked, possibly resulting in damage to the lead.

Figure 16:
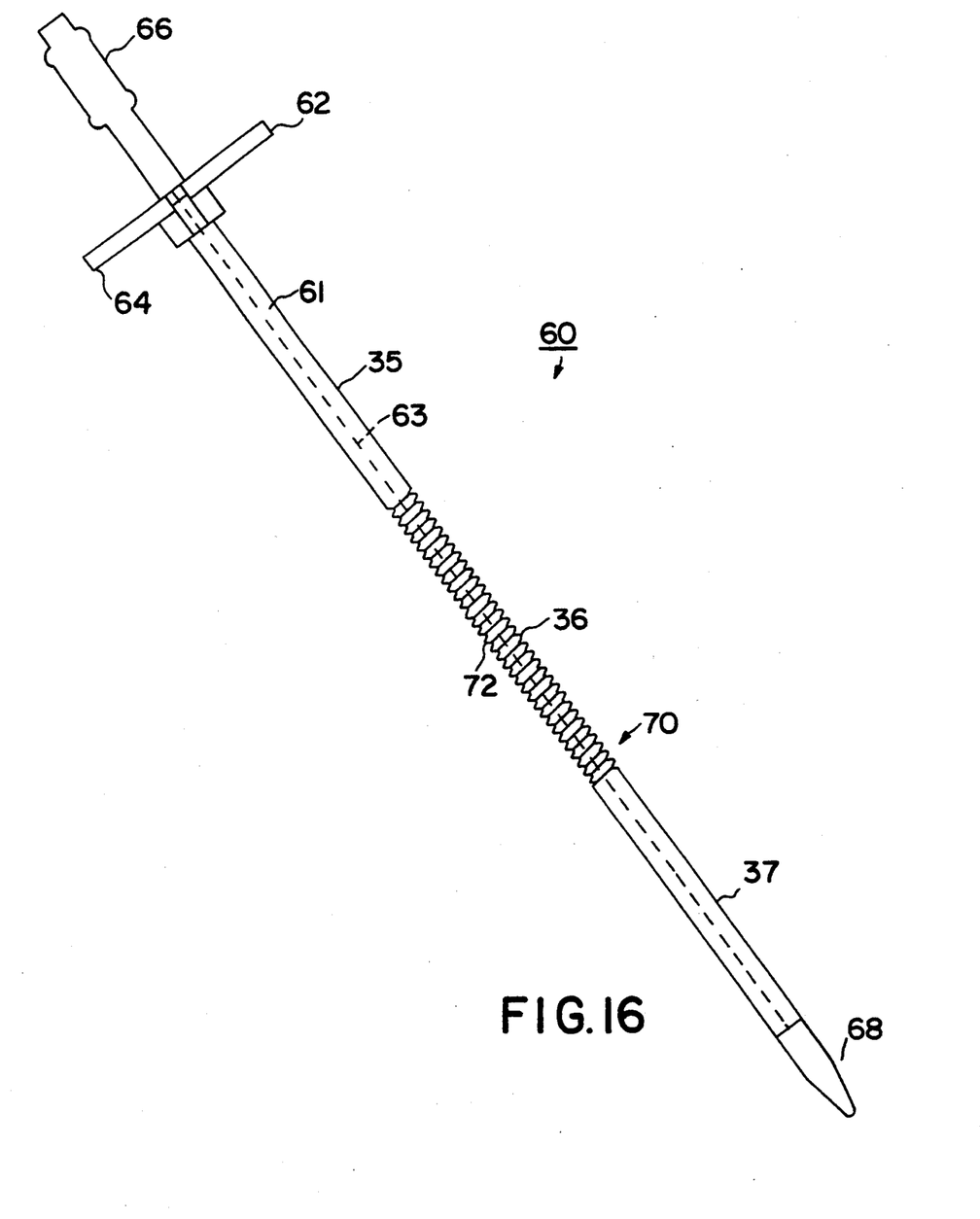
FIG. 16 depicts a lead introducer system in accordance with one embodiment of the present invention.

Turning now to FIG. 16, an introducer system 60 in accordance with one embodiment of the present invention is illustrated. Introducer system 60 comprises an introducer sheath 61 in which a vessel dilator 66 is inserted. tapered end 68 of vessel dilator 66 facilitates the introduction of sheath 60 into the subclavian vessel 24. Thereafter, guide wire 30 and vessel dilator 66 are withdrawn from the patient and central lumen 65 within sheath 61 provides access to the vessel 24.

In the embodiment of FIG. 16, sheath 61 includes means for permitting removal of sheath 61 from a lead disposed therethrough without requiring sheath 61 to be removed from an end of the lead. Specifically sheath 61 may be removed from a pacing lead by being longitudinally split apart along line 63. In particular, introducer sheath 61 is split apart by grasping tabs 62 and 64 as it is being withdrawn from the lead introduction site. In the preferred embodiment line 63 comprises a scoring within wall of sheath 63 as is well known in the art. Various other equivalent means may also be used to accomplish splitting sheath 61 along line 63, these include by providing a line of weakened wall, as shown in Vegoe et al U.S. Pat. No. 5,180,372, incorporated herein by reference, as well as providing a sheath slitter or the like, as is commonly known in the art. In addition, weakened section may consist of material having the physical property of molecular orientation whereby a tear in the material runs readily only in a longitudinal direction along the length of sheath 61, as is well known in the art.

Figure 17:
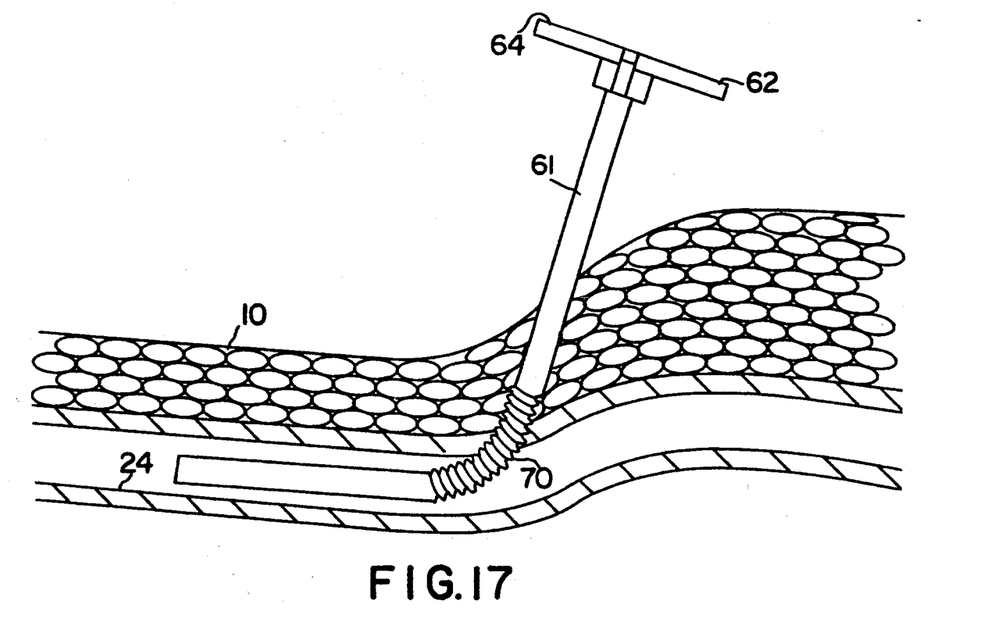
FIG. 17 depicts an introducer sheath of the present invention used in a body and not having a kink.

As seen in FIG. 16 kink resistant section 70 has a series of pleats 72. Pleats 72 permit kink resistant section 70 to bend more readily within a body 10 without the formation of kinks, as seen best seen in FIG. 17. Sheath 61 is preferably made from a biocompatible plastic, such as polytetrafluoroethylene. As seen sheath 60 has a proximal end having tabs 62, 64 and a distal end, through which introducer 68 extends. Sheath 60 further has proximal span 35, intermediate span 36 (having link resistant section 79) and distal span 37. Moreover, as seen proximal span 35 and distal span 37 have approximately equal lengths.

Figure 18:
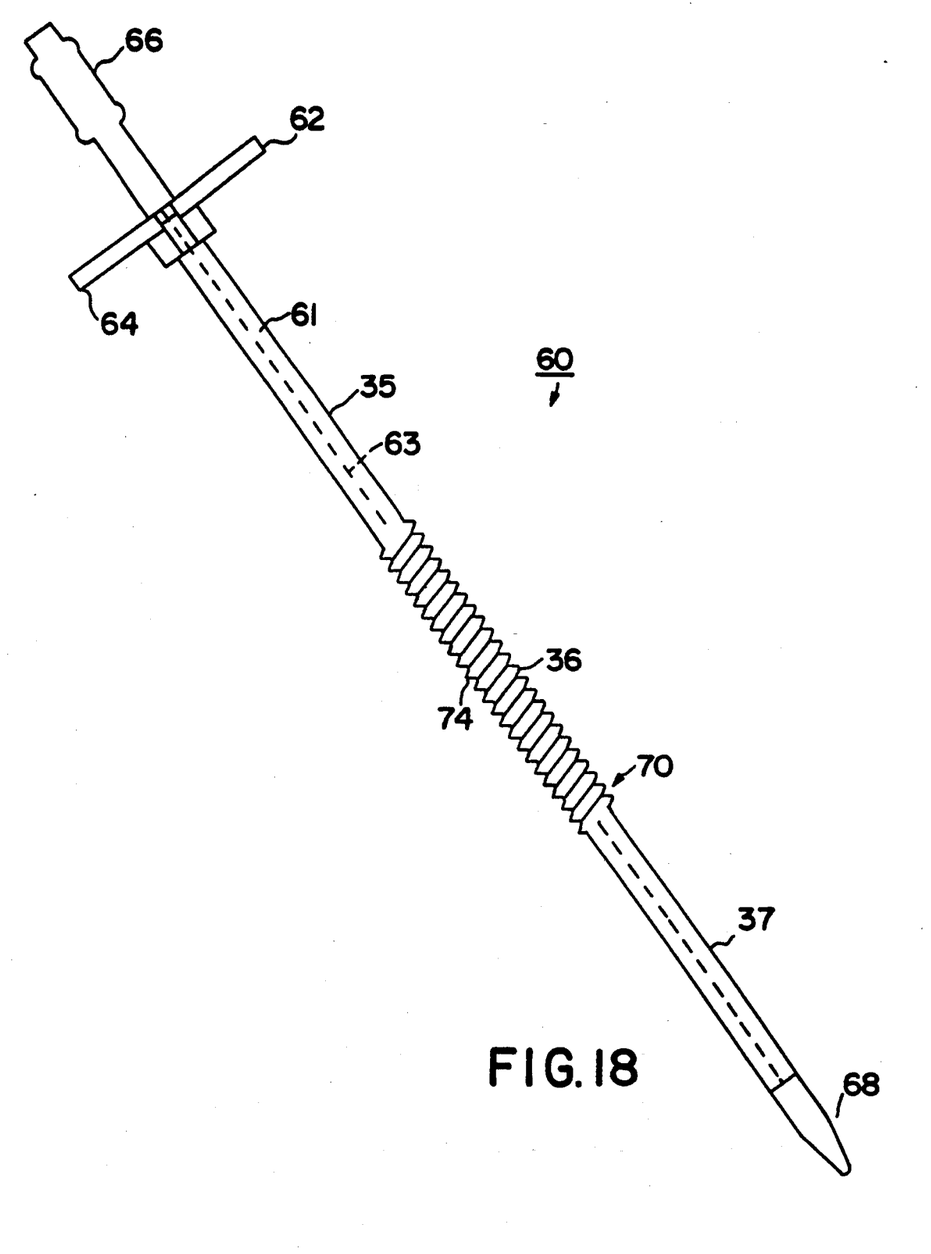
FIG. 18 depicts an alternate embodiment of a lead introducer system of the present invention.

FIG. 18 depicts an alternate embodiment of a lead introducer system of the present invention. As seen the introducer system 60 is substantially similar to that previously described with the exception that the kink resistant section 70 has a helical pleat 74. Helical pleat 74 forms a screw on the outer surface of sheath 61, thereby permitting sheath 61 to be screwed into tissue. As previously mentioned, on patients who have had multiple leads implanted scar tissue often covers the site of lead introduction and hampers implantation. Helical pleat 74 is believed to facilitate implantation by permitting sheath 61 to be screwed through scar tissue.

Figure 19:
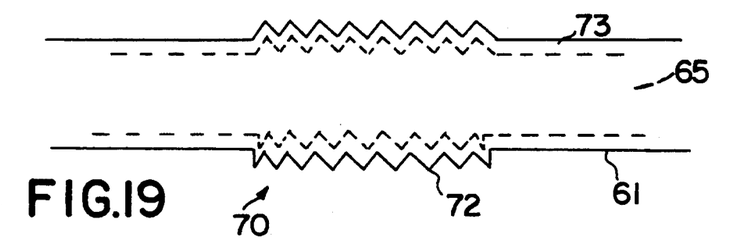
FIG. 19 is a detailed sectional view of a kink resistant section used in an introducer system of the present invention.

FIG. 19 is a detailed sectional view of kink resistant section 70 used in an introducer system of the present invention. As seen, pleats 72 extend throughout wall 73 of sheath 61.

Figure 20:
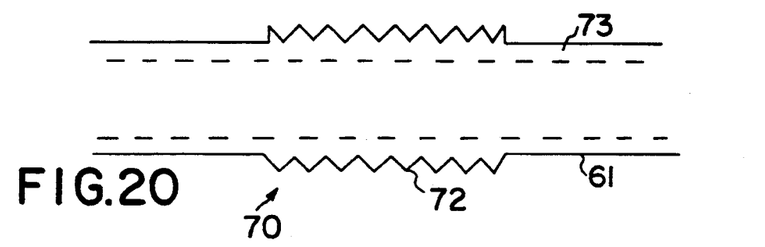
FIG. 20 is a detailed sectional view of an alternate embodiment of a kink resistant section used in an introducer system of the present invention.

An alternate embodiment of kink resistant section 70 used in an introducer system of the present invention is seen in FIG. 20. In this embodiment pleats 72 do not extend throughout wall 73 of sheath 61. As such the interior surface of sheath 61 is smooth along the kink resistant section 70. Such an embodiment is believed to facilitate passage of a lead therethrough.

Figure 21:
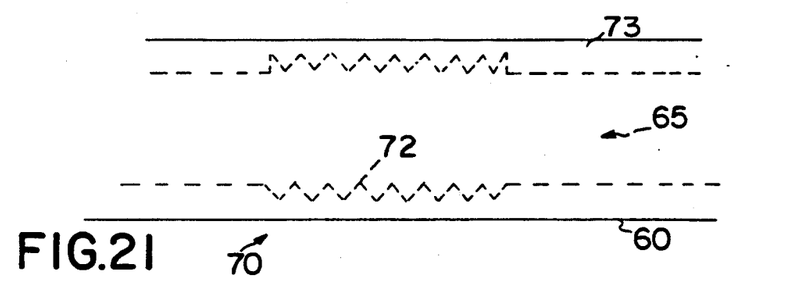
FIG. 21 is a detailed sectional view of an alternate embodiment of a kink resistant section used in an introducer system of the present invention.

FIG. 21 is a detailed sectional view of a still further alternate embodiment of a kink resistant section used in an introducer system of the present invention. This embodiment likewise features pleats 72 which do not extend throughout wall 73 of sheath 61. Pleats 72, however, are located within the inner wall of sheath 61. As such outer surface of sheath 61 is smooth along kink resistant section 70.

Figure 22:
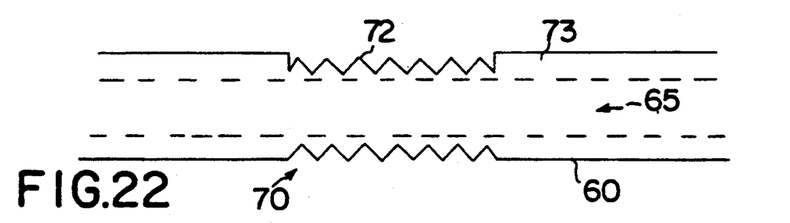
FIG. 22 is a detailed sectional view of an alternate embodiment of a kink resistant section used in an introducer system of the present invention.

FIG. 22 is a detailed sectional view of an alternate embodiment of a kink resistant section used in an introducer system of the present invention in which pleats 72 are recessed within outer surface of sheath 61.

Figure 23:
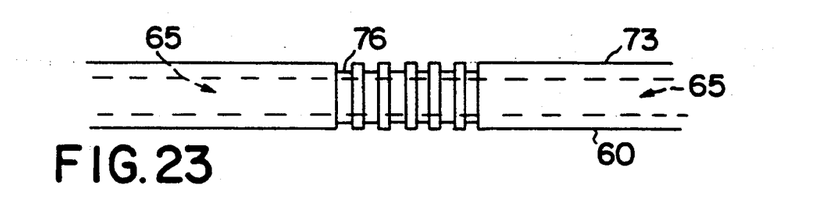
FIG. 23 is a detailed sectional view of an alternate embodiment of a kink resistant section used in an introducer system of the present invention.

FIG. 23 is a detailed sectional view of an alternate embodiment of a kink resistant section used in an introducer system of the present invention in which kink resistant section 70 has a series of grooves 76. Further alternate embodiments may feature other ways of accomplishing a kink resistant section as are well known in the art, such as a series of bellows or a corrugated surface, for example.

In the preferred embodiment, the introducer system of the present invention is sterilized using ethylene oxide and packaged as a kit with a sterilized percutaneous needle 28, a guide wire 30, and a dilator 42 in a hermetically sealed plastic bag (not shown.)

Figure 24:
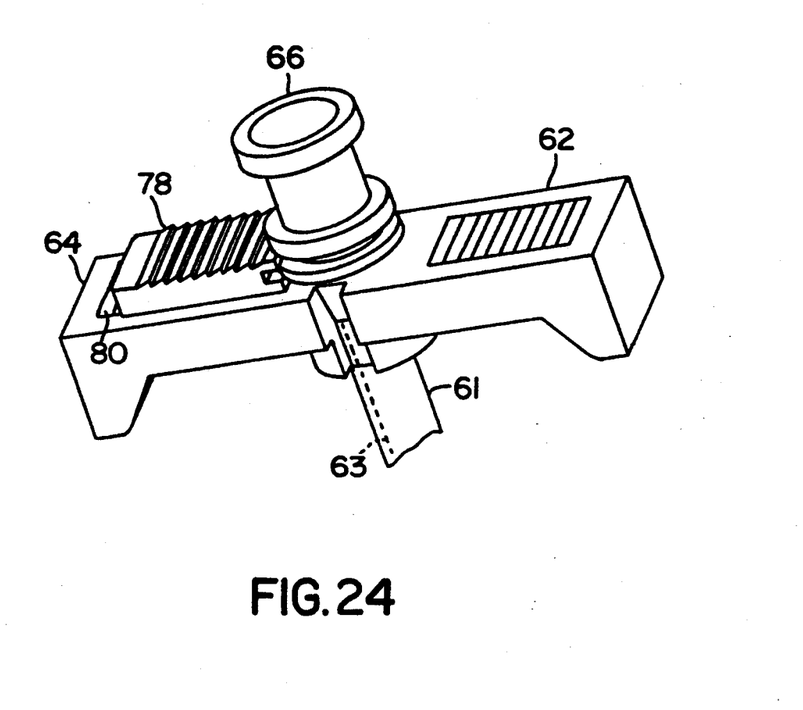
FIGS. 24 and 25 depict a detailed view of the distal end of an alternate embodiment of a lead introducer system featuring a sliding cap which may be incorporated with the present invention.
Figure 25:
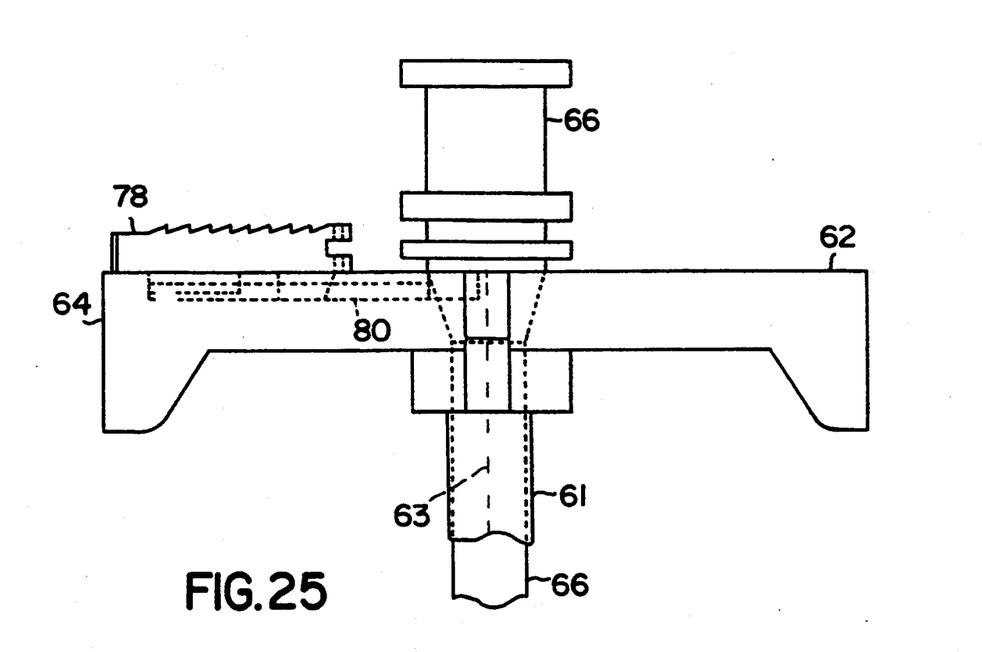

FIGS. 24 and 25 depict a still further alternate embodiment of the present invention. Specifically this embodiment features a device to inhibit blood flow through the sheath when a lead is not positioned within the lumen. As seen cap 78 is positioned within recess 80 so as to slide across the proximal end of sheath 61, and specifically between tabs 62 and 64, and cover the lumen within sheath 61 present when dilator 66 is withdrawn. Further details concerning the construction of such a device may be seen in the application of Pohndorf entitled "Lead Introducer with Mechanical Opening Valve" Ser. No. 07/865,578, filed Apr. 9, 1992 and incorporated herein by reference.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. An introducer system for use with a catheter or lead comprising:
    a sheath having a first end and a second end, said sheath being compatible for insertion within a body, said first end configured to insert said sheath within said body with said second end extending out of said body, said sheath having a central lumen configured to permit introduction of at least one lead or catheter therethrough;

a flexible kink resistant section located along said sheath;

means for permitting removal of said sheath from said lead or catheter disposed therethrough without requiring said sheath to be removed from an end of said lead or catheter disposed therethrough; and a dilator having a first end and a second end, said first end of said dilator being tapered, said dilator configured to be disposed through said central lumen of said sheath.

2. The introducer system of claim 1 wherein said means for permitting removal of said sheath comprises means for splitting said sheath away from said lead or catheter disposed therethrough.

3. The introducer system of claim 2 wherein said means for splitting said sheath comprise a first tab on a first side of said second end of said sheath, and a second tab on a second side of said second end of said sheath whereby, when said tabs are pulled apart, said sheath tears longitudinally separating said sheath from said lead or catheter disposed therethrough.

4. The introducer system of claim 2 wherein said means for splitting said sheath comprises a weakened section extending longitudinally from said first end to said second end of said sheath.

5. The introducer system of claim 4 wherein said weakened section comprises a score line.

6. The introducer system of claim 4 wherein said weakened section comprises a section of material having the physical property of molecular orientation whereby a tear in said material runs readily only in a longitudinal direction along the length of said sheath.

7. The introducer system of claim 1 wherein said flexible kink resistant section is smooth on its outer surface permitting said sheath to be slid through tissue of said body.

8. The introducer system of claim 1 wherein said flexible kink resistant section comprises a helical pleat on said outer surface of said sheath, said helical pleat permitting a portion of said sheath to be screwed through tissue of said body.

9. The introducer system of claim 1 further comprising said flexible kink resistant section being continuously smooth on its inner surface.

10. The introducer system of claim 1 further comprising said flexible kink resistant section comprising at least two pleats on said inner surface to increase the flexibility of said section.

11. The introducer system of claim 1 further comprising said flexible kink resistant section comprising at least two pleats on said outer surface to increase the flexibility of said section.

12. The introducer system of claim 1 further comprising said flexible kink resistant section comprising at least two pleats on said outer surface and further comprising at least two pleats on said inner surface.

13. The introducer system of claim 1 wherein said flexible kink resistant section comprises a series of bellows.

14. The introducer system of claim 1 in which the material is a plastic.

15. The introducer system of claim 1 in which the material is polytetrafluoroethylene.

16. The introducer system of claim 1 in which said first end of said sheath is tapered so as to define a tapered end portion, said sheath having an inner surface and an outer surface and having a substantially uniform thickness from the inner surface to the outer surface except at the tapered end portion and the flexible kink resistant section.

17. An introducer system for use with a catheter or lead comprising:

a sheath having a first end and a second end, said sheath further having a proximal span, an intermediate span and a distal span, said proximal span and said distal span having approximately equal length, said first end having means for inserting said sheath within said body with said second end extending out of said body, said sheath having a central lumen configured to permit introduction of at least one lead or catheter therethrough;

a flexible kink resistant section located along said intermediate span;

means for permitting removal of said sheath from said lead or catheter disposed therethrough without requiring said sheath to be removed from an end of said lead or catheter disposed therethrough; and a dilator having a first end and a second end, said first end of said dilator being tapered, said dilator disposed through said central lumen of said sheath.

18. The introducer system of claim 17 wherein said means for permitting removal of said sheath comprises means for splitting said sheath away from said lead or catheter disposed therethrough.

19. The introducer system of claim 18 wherein said means for splitting said sheath comprise a first tab on a first side of said second end of said sheath, and a second tab on a second side of said second end of said sheath whereby, when said tabs are pulled apart, said sheath tears longitudinally separating said sheath from said lead or catheter disposed therethrough.

20. The introducer system of claim 18 wherein said means for splitting said sheath comprises a weakened section extending longitudinally from said first end to said second end of said sheath.

21. The introducer system of claim 20 wherein said weakened section comprises a score line.

22. The introducer system of claim 20 wherein said weakened section comprises a section of material having the physical property of molecular orientation whereby a tear in said material runs readily only in a longitudinal direction along the length of said sheath.

23. The introducer system of claim 17 wherein said flexible kink resistant section is smooth on its outer surface permitting said sheath to be slid through tissue of said body.

24. The introducer system of claim 17 wherein said flexible kink resistant section comprises a helical pleat on said outer surface of said sheath, said helical pleat permitting a portion of said sheath to be screwed through tissue of said body.

25. The introducer system of claim 17 further comprising said flexible kink resistant section being continuously smooth on its inner surface.

26. The introducer system of claim 17 further comprising said flexible kink resistant section comprising at least two pleats on said inner surface to increase the flexibility of said section.

27. The introducer system of claim 17 further comprising said flexible kink resistant section comprising at least two pleats on said outer surface to increase the flexibility of said section.

28. The introducer system of claim 17 further comprising said flexible kink resistant section comprising at least two pleats on said outer surface and further comprising at least two pleats on said inner surface.

29. The introducer system of claim 17 wherein said flexible kink resistant section comprises a series of bellows.

30. The introducer system of claim 17 in which the material is a plastic.

31. The introducer system of claim 17 in which the material is polytetrafluoroethylene.

32. The introducer system of claim 17 in which said first end of said sheath is tapered so as to define a tapered end portion, said sheath having an inner surface and an outer surface and having a substantially uniform thickness from the inner surface to the outer surface except at the tapered end portion and the flexible kink resistant section.

33. The introducer system of either claims 1 or 17 further comprising means for inhibiting blood flow through said sheath positioned on a proximal end of said sheath.

34. A method of introducing a body implantable lead comprising the steps of:
   introducing a percutaneous needle having a central lumen through a patient's skin and into said patient's blood vessel;
   introducing a wire guide through said central lumen and into said patient's blood vessel;
   providing a rigid dilator through a lumen of an introducer sheath having a kink resistant section;
   introducing said rigid dilator and introducer sheath into said patient's blood vessel a first distance, wherein said introducer sheath is straight;
   withdrawing said rigid dilator from said lumen of said introducer sheath;
   introducing said introducers sheath from said first distance, wherein said rigid dilator and introducer sheath are straight, to a second distance within said patient's blood vessel, wherein said introducer sheath is bent at along said kink resistant section; and
   introducing a body implantable lead through said introducer sheath into said patient's blood vessel.

35. The method according to claim 34 further comprising the step of removing said introducer sheath from said patient's blood vessel without removing said sheath from over an end of said lead.

36. A method of introducing a body implantable lead comprising the steps of:
   introducing a percutaneous needle having a central lumen through a patient's skin and into said patient's blood vessel;
   introducing a wire guide through said central lumen and into said patient's blood vessel;
   providing a rigid dilator through a lumen of an introducer sheath having a bellowed section;
   introducing said rigid dilator and introducer sheath into said patient's blood vessel a first distance, wherein said introducer sheath is straight;
   withdrawing said rigid dilator from said lumen of said introducer sheath;
   introducing said introducer sheath from said first distance, wherein said rigid dilator and introducer sheath are straight, to a second distance into said patient's blood vessel wherein said introducer sheath is bent along said bellowed section;
   introducing a body implantable lead through said introducer sheath into said patient's blood vessel; and
   removing said introducer sheath from said patient's blood vessel without removing said sheath from over an end of said lead.

37. The method of either claims 34 or 36 further comprising the step of providing on a proximal end of said sheath means for inhibiting blood flow through said sheath.

* * * * *